United States Patent
Laskoski et al.

(10) Patent No.: US 9,394,404 B2
(45) Date of Patent: Jul. 19, 2016

(54) SYNTHESIS AND POLYMERIZATION OF OLIGOMERIC ALIPHATIC-AROMATIC BASED PHTHALONITRILES

(71) Applicant: The United States of America, as represented by the Secretary of the Navy, Washington, DC (US)

(72) Inventors: Matthew Laskoski, Springfield, VA (US); Teddy M. Keller, Fairfax Station, VA (US); Andrew P. Saab, Washington, DC (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/968,099

(22) Filed: Dec. 14, 2015

(65) Prior Publication Data

US 2016/0168326 A1    Jun. 16, 2016

Related U.S. Application Data

(60) Provisional application No. 62/092,291, filed on Dec. 16, 2014.

(51) Int. Cl.
| | | |
|---|---|---|
| C08G 63/02 | (2006.01) | |
| C08G 65/40 | (2006.01) | |
| C07C 255/54 | (2006.01) | |
| C07C 253/30 | (2006.01) | |
| C07F 7/08 | (2006.01) | |

(52) U.S. Cl.
CPC .......... *C08G 65/4006* (2013.01); *C07C 253/30* (2013.01); *C07C 255/54* (2013.01); *C07F 7/0854* (2013.01); *C07F 7/0889* (2013.01)

(58) Field of Classification Search
CPC ......... C08G 73/00; C08G 73/06; C08G 63/19
USPC ........................... 528/193, 194, 271, 272, 279
See application file for complete search history.

(56) References Cited

U.S. PATENT DOCUMENTS

| | | | |
|---|---|---|---|
| 4,200,728 A | 4/1980 | Blinne et al. | |
| 4,209,458 A | 6/1980 | Keller et al. | |
| 4,408,035 A | 10/1983 | Keller | |
| 4,409,382 A | 10/1983 | Keller | |
| 4,410,676 A | 10/1983 | Keller | |
| 4,619,986 A | 10/1986 | Keller | |
| 5,003,039 A | 3/1991 | Keller | |
| 5,003,078 A | 3/1991 | Keller | |
| 5,004,801 A | 4/1991 | Keller et al. | |
| 5,104,559 A | 4/1992 | Pawloski et al. | |
| 5,132,396 A | 7/1992 | Keller | |
| 5,159,054 A | 10/1992 | Keller | |
| 5,202,414 A | 4/1993 | Keller et al. | |
| 5,208,318 A | 5/1993 | Keller | |
| 5,237,045 A | 8/1993 | Burchill et al. | |
| 5,247,060 A | 9/1993 | Keller | |
| 5,262,514 A | 11/1993 | Keller | |
| 5,292,854 A | 3/1994 | Keller | |
| 5,304,625 A | 4/1994 | Keller | |
| 5,350,828 A | 9/1994 | Keller et al. | |
| 5,352,760 A | 10/1994 | Keller | |
| 5,389,441 A | 2/1995 | Keller | |
| 5,464,926 A | 11/1995 | Keller | |
| 5,895,726 A | 4/1999 | Imam et al. | |
| 5,925,475 A | 7/1999 | Sastri et al. | |
| 5,939,508 A | 8/1999 | Keller | |
| 5,965,268 A | 10/1999 | Sastri et al. | |
| 5,980,853 A | 11/1999 | Keller et al. | |
| 6,001,926 A | 12/1999 | Sastri et al. | |
| 6,297,298 B1 | 10/2001 | Keller et al. | |
| 6,756,470 B2 | 6/2004 | Keller et al. | |
| 6,891,014 B2 | 5/2005 | Keller et al. | |

(Continued)

FOREIGN PATENT DOCUMENTS

| | | |
|---|---|---|
| GB | 1078234 A | 8/1967 |
| JP | 06-128372 | 5/1994 |
| JP | 06-256499 | 9/1994 |
| JP | 06-263864 | 9/1994 |
| JP | 06-298923 | 10/1994 |
| JP | 2002105070 A | 4/2002 |
| SU | 1509352 A1 | 9/1989 |

OTHER PUBLICATIONS

McKeown et al., "Towards Phthlalocyanine Network Polymers for Heterogeneous Catalysis" ChemInform 32(48), 214-218 (2001).

(Continued)

*Primary Examiner* — Terressa Boykin
(74) *Attorney, Agent, or Firm* — US Naval Research Laboratory; Joseph T. Grunkemeyer

(57) ABSTRACT

A phthalonitrile compound having the formula below. The value n is a positive integer. Each R has a hydrocarbon chain optionally having —O— or —SiR'$_2$—O—. Each R' is an aliphatic group. Each Ar is an aromatic group with the proviso that Ar contains at least two aromatic rings when n is 1 and R is an alkylene group. A method of: reacting an excess of a dihydroxyaromatic compound with a dihalocompound to form an oligomer; and reacting the oligomer with 4-nitrophthalonitrile to form the phthalonitrile compound, where Ar is an aromatic group.

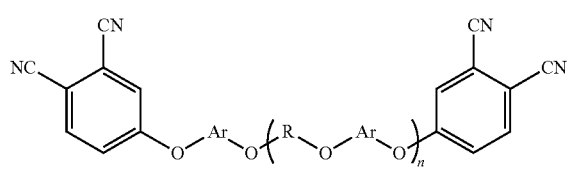

20 Claims, 4 Drawing Sheets

(56) References Cited

U.S. PATENT DOCUMENTS

| | | |
|---|---|---|
| 7,087,707 B2 | 8/2006 | Keller et al. |
| 7,342,085 B2 | 3/2008 | Keller et al. |
| 7,348,395 B2 | 3/2008 | Keller et al. |
| 7,452,959 B2 | 11/2008 | Keller et al. |
| 7,511,113 B2 | 3/2009 | Keller et al. |
| 7,723,420 B2 | 5/2010 | Laskoski et al. |
| 7,897,715 B1 | 3/2011 | Laskoski et al. |
| 8,039,576 B2 | 10/2011 | Laskoski et al. |
| 8,222,403 B2 | 7/2012 | Laskoski et al. |
| 8,288,454 B2 | 10/2012 | Keller et al. |
| 8,362,239 B2 | 1/2013 | Laskoski et al. |
| 8,735,532 B2 * | 5/2014 | Keller ............ C08G 73/024 427/412.1 |
| 8,859,712 B2 | 10/2014 | Keller et al. |
| 8,921,510 B1 | 12/2014 | Keller et al. |
| 8,981,036 B2 | 3/2015 | Keller et al. |
| 2014/0275472 A1 * | 9/2014 | Keller ............ C08G 65/40 528/362 |
| 2015/0065713 A1 | 3/2015 | Banning et al. |

OTHER PUBLICATIONS

Rodríguez-Morgade et al., "Design and Synthesis of Low-Symmetry Phthalocyanines and Related Systems" The Porphyrin Handbook 15, 125-160 (2003).

Sastri et al., "Phthalonitrile Cure Reaction with Aromatic Diamines" Journal of Polymer Science: Part A: Polymer Chemistry, vol. 36, 1885-1890 (1998).

Sastri et el., "Phthalonitrile-Carbon Fiber Composites" Polymer Composites, Dec. 1996, vol. 17, No. 6.

Takagi et al., "Flying-seed-like liquid crystals 2: unprecedented guidelines to obtain liquid crystalline compounds" J. Mater. Chem., 2012, 22, 14418.

Tolbin et al., "Bi- and polynuclear phthalocyanines: synthesis and study of physicochemical properties" Russian Chemical Reviews 77(5) 435-449 (2008).

Eastmond et al., "Polyimides with main-chain ethylene oxide units: synthesis and properties" Polymer 43 (2002) 3455-3468.

Laskoski et al., "Oligomeric Aliphatic-Aromatic Ether Containing Phthalonitrile Resins" J. Polym. Sci. A: Polym. Chem. 2015, 53, 2186-2191.

Xu et al., "Design of low temperature self-cured phthalonitrile-based polymers for advanced glass fiber composite aminates" J. Mater. Sci. (2013) 48:8108-8116.

Search Report and Written Opinion in PCT/US2015/065675 (Apr. 1, 2016).

* cited by examiner

SYNTHESIS AND POLYMERIZATION OF OLIGOMERIC ALIPHATIC-AROMATIC BASED PHTHALONITRILES

This application claims the benefit of U.S. Provisional Application No. 62/092,291, filed on Dec. 16, 2014. The provisional application and all other publications and patent documents referred to throughout this nonprovisional application are incorporated herein by reference.

TECHNICAL FIELD

The present disclosure is generally related to phthalonitrile compounds.

DESCRIPTION OF RELATED ART

Phthalonitrile resins are showing outstanding potential as matrix materials for advanced composites. Phthalonitrile monomers polymerize through the cyano groups, with the aid of an appropriate curing agent, to yield a crosslinked polymeric network with high thermal and oxidative stabilities. These polymers are obtained by heating the phthalonitrile monomers and a small amount of curing additive in the melt-state for extended periods of time at elevated temperatures. A variety of phthalonitrile monomers containing aromatic ether, thioether, imide, and sulfone linkages between the terminal phthalonitrile units have been synthesized and cured or converted to crosslinked/networked polymers. The cure reaction of these monomers have been investigated using a variety of curing additives such as organic amines, strong organic acids, strong organic acids/amine salts, metallic salts and metals. When postcured at elevated temperatures at about 400° C., the thermoset shows excellent long-term thermal and oxidative stabilities to temperatures approaching 375° C. In addition, the high aromatic content of the thermoset affords a high char yield (60-90%) when pyrolyzed to 1000° C. under inert conditions. The high thermal stability and the ability to form a high char yield upon pyrolysis contribute to the outstanding fire performance of the phthalonitrile polymer. For instance, the fire performance of phthalonitrile-carbon and phthalonitrile-glass composites are superior to that of other thermoset-based composites currently in use for aerospace, ship and submarine applications. The phthalonitriles are still the only polymeric material that meets MIL-STD-2031 for usage inside of a submarine.

Current phthalonitrile research efforts are targeted towards developing high temperature and flame resistant composites and addressing composite processability based on cost effective on manufacturing techniques such as resin transfer molding (RTM), resin infusion molding (RIM), and filament winding. One of the objectives has been concerned with the incorporation of units within the backbone to improve on the synthesis at lower temperatures and to enhance the flammability resistance and thermo-oxidative properties while retaining low temperature processability. A low viscosity resin enables composite processing by RTM and RIM manufacturing methods. Furthermore, a low melt viscosity and a larger processing window are useful for fabrication of thick composite sections where the melt has to impregnate thick fiber preforms. Low melting oligomeric phthalonitrile monomers and curing additives that do not volatilize at elevated cure reaction temperatures such as bis[4-(4-aminophenoxy) phenyl]sulfone (p-BAPS) have been shown to enhance the overall physical properties and processability of phthalonitrile-based composites.

BRIEF SUMMARY

Disclosed herein is a phthalonitrile compound having the formula below. The value n is a positive integer. Each R comprises a hydrocarbon chain optionally comprising —O— or —SiR'$_2$—O—. Each R' is an aliphatic group. Each Ar is an aromatic group with the proviso that Ar comprises at least two aromatic rings when n is 1 and R is an alkylene group.

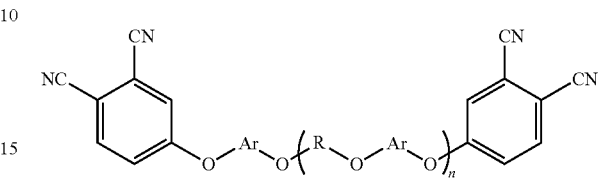

Also disclosed herein is a method comprising: reacting an excess of a dihydroxyaromatic compound having the formula HO—Ar—OH with a dihalocompound having the formula X—R—X to form an oligomer; and reacting the oligomer with 4-nitrophthalonitrile to form a phthalonitrile compound having the formula above. Each X is a halide, R is as defined above, and each Ar is an aromatic group.

BRIEF DESCRIPTION OF THE DRAWINGS

A more complete appreciation will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed herein the synthesis and polymerization of low melting oligomeric phthalonitrile monomers containing multiple aromatic ether and aliphatic moieties between the terminal phthalonitrile units. The novel oligomeric aromatic ether-aliphatic-containing phthalonitrile monomers can polymerize through the phthalonitrile units to afford high temperature, flame resistant thermosets. Desirable physical properties such as a low glass transition (T$_g$) temperature and high thermal and oxidation stability can be obtained at lower postcure temperatures (~300° C.). Polymeric composites and coatings formulated from the new phthalonitriles should have outstanding thermo-oxidative and flammability properties for ship, submarine, and aerospace applications and can withstand continuous high temperatures (300-375° C.) in oxidative environments such as air for extended periods. To date, current oligomeric phthalonitrile polymers have melting points between 50 and 100° C. with the polymerization occurring in excess of 200° C. The use of low molecular weight precursor resins to obtain thermosetting polymeric materials with high thermo-oxidative properties is often advantageous from a processing standpoint. Precursor resins are useful in composite fabrication by a variety of methods such as infusion, resin transfer molding, and prepreg consolidation. The phthalonitriles may be suitable for numerous aerospace and electronic applications due to their outstanding and superior thermal and oxidative properties, ease of processability, and low water absorption relative to other high temperature polymers such as polyimides. Furthermore, resins with a large window between the melting point and the cure temperature are desirable to control the viscosity and the rate of curing. With these disclosed phthalonitrile monomers, processability to shaped composite components may be achieved in non-autoclave conditions potentially above 70° C. and by cost effective methods.

Figure 1:
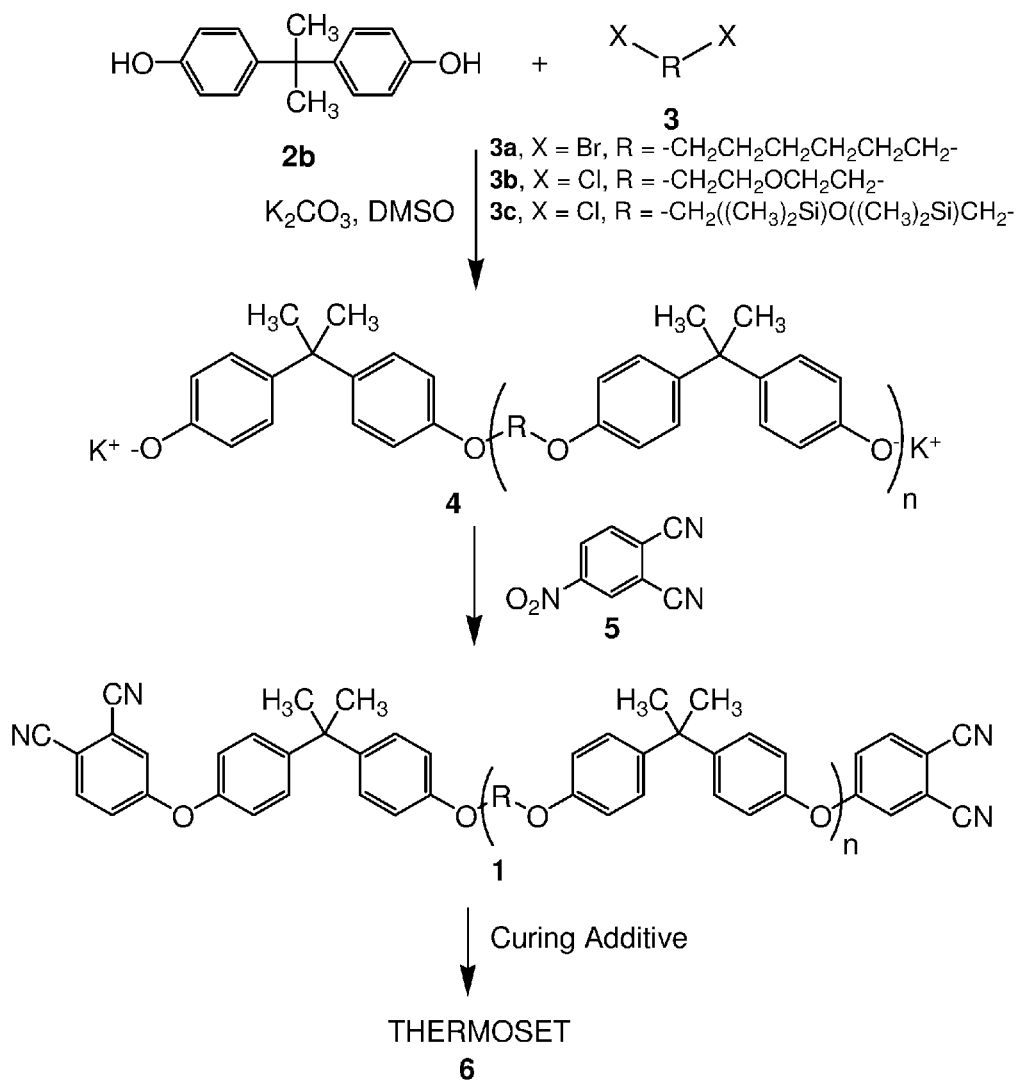
FIG. 1 shows the synthesis of oligomer phthalonitrile 1 and thermoset 6.
Figure 2:
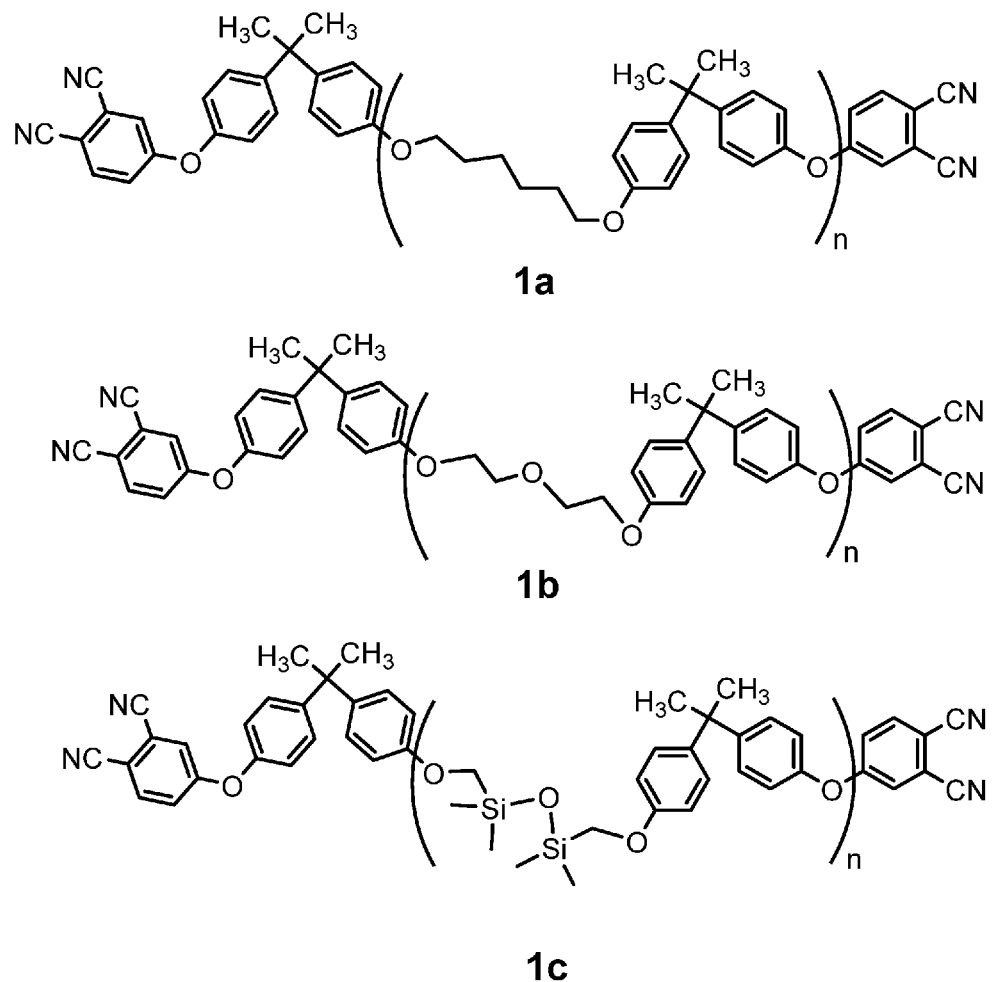
FIG. 2 shows the structures of phthalonitriles 1a, 1b, and 1c.

Earlier simple bisphenol-based phthalonitriles had melting points in excess of 200° C. It was, therefore, desirable to design and prepare low melting oligomeric phthalonitrile monomers, which upon polymerization would retain the useful thermal properties (300-375° C.) exhibited by the phthalonitrile polymers but with greater thermo-oxidative and superior flammability properties. Such monomers should also exhibit a large processing window useful for composite and device fabrication. The term "oligomeric" means that more than one compound is formed during the synthesis of 1 (FIG. 1) with the average molecular weight dependent on the ratios of reactants, 2 and 3, used. The synthesis of a series of multiple aromatic ether-linked phthalonitriles 1, which contain aryl ether and aliphatic units in the backbone, has been achieved by a one pot reaction involving initially a nucleophilic displacement reaction between bisphenol A 2, dihaloaliphatic compound 3, under basic conditions ($K_2CO_3$) in dimethylsulfoxide (DMSO) at temperatures around 90° C. (FIG. 1). Once NMR spectroscopy confirmed the desired oligomeric diphenolate product 4, the displacement reaction was considered complete. Further reaction of 4 with 4-nitrophthalonitrile 5 afforded the oligomeric phthalonitriles 1, which were readily soluble in common organic solvents such as toluene, DMF, acetone, methylene chloride, ether, and chloroform, in 91-95% yields. The structure of the phthalonitrile monomers 1 was confirmed by IR and $^1$H-NMR spectroscopy. The length of the spacer between the terminal phthalonitrile groups can be varied by changing the ratio between 2 (excess) and 3. Oligomeric phthalonitrile resins 1 generally have melting point between 50 and 70° C. Several oligomeric phthalonitriles 1 have been synthesized by this method and the structures of 1a, 1b, and 1c are shown in FIG. 2.

Figure 3:
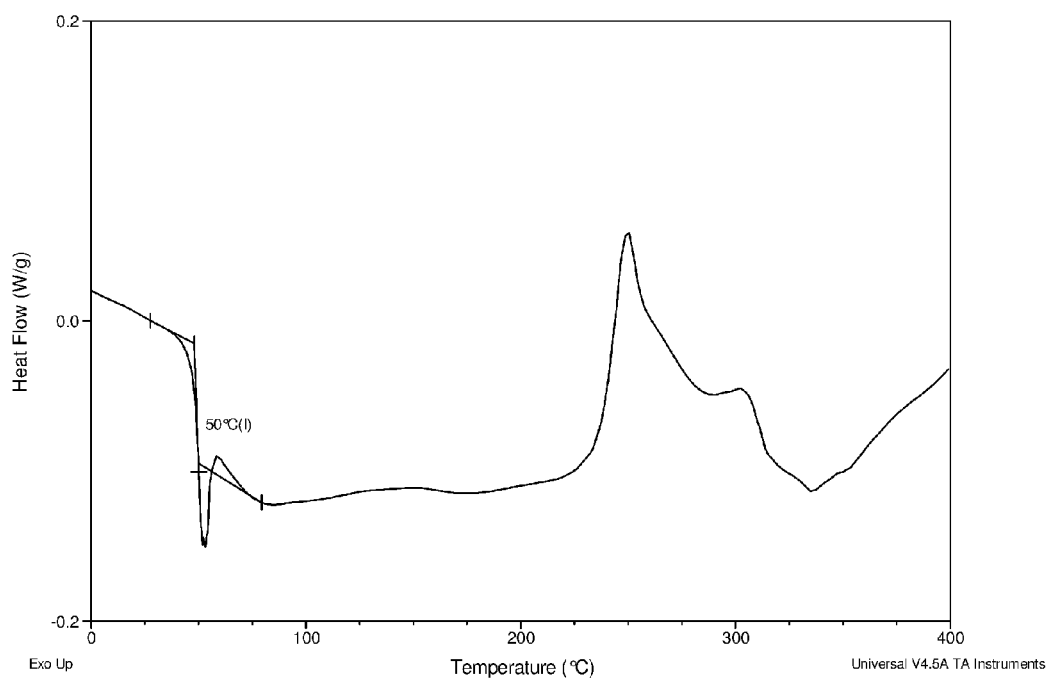
FIG. 3 shows the DSC thermograms of phthalonitrile resin 1a cured with 10 mol % of m-BAPS.

Polymerization studies of phthalonitrile 1 (n=1) were achieved by DSC analyses up to 400° C. in the presence of 3 weight % of bis(3-[4-aminophenoxy]phenyl)sulfone (m-BAPS) to afford thermosets 6. Using a resin 1a as an example, the DSC thermogram (FIG. 3) revealed an endothermic transition (glass transition temperature ($T_g$)) at approximately 50° C. and an exothermic transition peaking at 250° C. attributed to the reaction with m-BAPS. Therefore, 1a exhibited low softening temperatures was completely free flowing above 50° C. as determined by a visual melting test and DSC analysis and had a long processing window (~100° C.) before reaction with the curing additive started to occur above 150° C. The polymerization studies of 1b and 1c displayed similar DSC thermograms as 1a.

Figure 4:
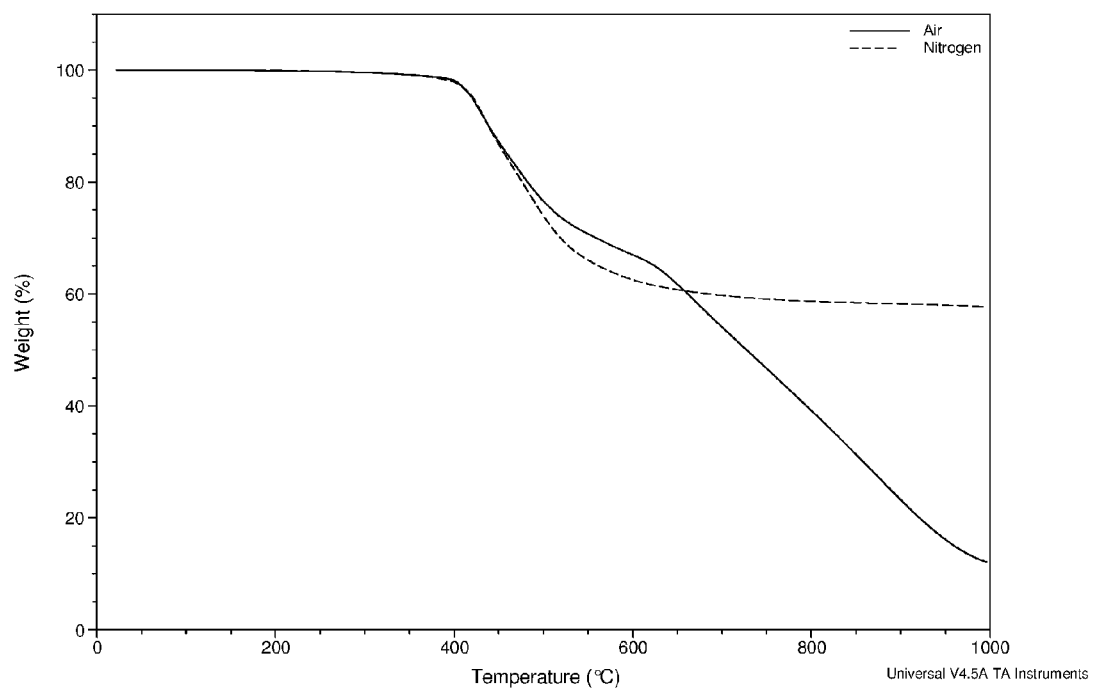
FIG. 4 shows TGA thermograms of bisphenol A siloxane phthalonitrile resin 6c heated under air and nitrogen atmospheres.

Low molecular weight diaryl ether aliphatic-containing compounds 4 were used in the preparation of novel oligomeric phthalonitriles 1. The oligomeric phthalonitriles 1 were easily converted to polymer 6 under thermal conditions and in the presence of a curing additive. Under these curing conditions, the new phthalonitrile monomer 1 offers a broad processing window, which is important for the fabrication of complex shaped composite components. The thermosets or cured polymers 6 show outstanding and superior thermo-oxidative properties. FIG. 4 shows TGA thermograms of the bisphenol A derived phthalonitrile thermoset 1c containing a siloxane moiety between the phthalonitrile end groups that has been heated to 1000° C. The polymer 6c exhibits thermal and oxidative stability to about 400° C. before any significant weight loss occurred. Table 1 shows the rheometric viscosity for all three new phthalonitriles (1a-1c). Upon heating 1a to 100° C., a viscosity of 2,000 cP was observed (Table 1). Further heating precipitously decreased the viscosity to 300 cP at 150° C. and to 70 cP at 200° C. Similar viscosities were observed for the other two PN resins. These viscosity values afford an optimal processing window, a distinguishing feature necessary for the molding of complex shapes using RTM or related composite processing methods. Due to the superb thermal and oxidative stability of phthalonitrile polymers 6 cured to 400° C., the materials have potential for a variety of applications (ship, aerospace, marine, and electronic) including its use in the fabrication of advanced composites by conventional prepreg consolidation, RTM, RIM, injection molding, and filament winding and as a coating for electronic devices. Thus, the phthalonitrile-based polymers would be expected to exhibit improvements in specific physical properties when used at high temperatures or in a fire environment.

TABLE 1

Viscosity data for monomers 1a-1c

| Temperature (° C.) | Viscosity (cP) | | |
| --- | --- | --- | --- |
| | 1a | 1b | 1c |
| 100 | 2000 | 2000 | 1400 |
| 125 | 600 | 600 | 350 |
| 150 | 300 | 120 | 180 |
| 175 | 90 | 75 | 100 |
| 200 | 70 | 45 | 50 |
| 225 | 50 | 35 | 30 |
| 250 | 40 | 30 | 20 |

This is the first reported synthesis of oligomeric compounds 4, conversion to low melting oligomeric phthalonitriles 1, and polymerization to thermosetting polymer 6 with a large processing window between the melting point and the exothermic curing temperature. The phthalonitrile monomers 1, which display superb processability, can be readily cross-linked through the phthalonitrile groups yielding high temperature thermosetting polymers. The synthesis of a series of multiple aromatic ether-linked phthalonitriles 1, which contain an aryl ether and aliphatic units in the backbone, has been achieved by a nucleophilic displacement reaction utilizing a dihaloaliphatic compound 3 and bisphenol A 2 followed by end-capping with 4-nitrophthalonitrile 5 (FIG. 1). Other dihaloaliphatic compound and bisphenols can be used in the synthesis.

The method involves the formation of a phthalonitrile compound, including diphthalonitrile compounds, from a dihydroxyaromatic compound and a dihalo compound. The dihydroxyaromatic compound has the formula HO—Ar—OH, where Ar is an aromatic group. The Ar group can be any divalent radical with or without substituents containing one or more fused aromatic rings, one or more non-fused aromatic rings with or without intervening functional groups, or combinations thereof wherein the hydroxyl groups are on the same or different aromatic rings. Suitable dihydroxyaromatic compounds include those shown in Table 2, as well as those disclosed in U.S. Pat. No. 3,730,946, U.S. Pat. No. 3,763,210, U.S. Pat. No. 3,787,475, U.S. Pat. No. 3,869,499, U.S. Pat. No. 3,972,902, U.S. Pat. No. 4,209,458, U.S. Pat. No. 4,223,123, U.S. Pat. No. 4,226,801, U.S. Pat. No. 4,234,712, U.S. Pat. No. 4,238,601, U.S. Pat. No. 4,259,471, U.S. Pat. No. 4,304,896, U.S. Pat. No. 4,307,035, U.S. Pat. No. 4,315,093, U.S. Pat. No. 4,351,776, U.S. Pat. No. 4,408,035, U.S. Pat. No. 4,409,382, U.S. Pat. No. 4,410,676, U.S. Pat. No. 5,003,039, U.S. Pat. No. 5,003,078, U.S. Pat. No. 5,004,801, U.S. Pat. No. 5,132,396, U.S. Pat. No. 5,159,054, U.S. Pat. No. 5,202,414, U.S. Pat. No. 5,208,318, U.S. Pat. No. 5,237,045, U.S. Pat. No. 5,242,755, U.S. Pat. No. 5,247,060, U.S. Pat. No. 5,292,854, U.S. Pat. No. 5,304,625, U.S. Pat. No. 5,350,828, U.S. Pat. No. 5,352,760, U.S. Pat. No. 5,389,441, U.S. Pat. No. 5,464,926, U.S. Pat. No. 5,925,475, U.S. Pat. No. 5,965,268, U.S. Pat. No. 6,001,926, U.S. Pat. No. 6,297,298, U.S. Pat. No. 6,756,470, U.S. Pat. No. 6,891,014, U.S. Pat. No. 7,452,959, U.S. Pat. No. 7,511,113, U.S. Pat. No. 8,039,576, U.S. Pat. No. 8,222,403, U.S. Pat. No. 8,362,239, U.S. Pat. No. 8,530,607, U.S. Pat. No. 8,735,532, U.S. Pat. No. 8,859,712, U.S. Pat. No. 8,981,036, U.S. Pat. No. 8,921,510, and U.S. patent application Ser. No. 14/926,429, all incorporated herein by reference. The Ar group may include at least two aromatic rings, either fused or non-fused as in bisphenols.

TABLE 2

| Name | Structure |
|---|---|
| bisphenol A (2,2-bis(4-hydroxyphenyl)propane) | HO—⌬—C(CH₃)₂—⌬—OH |
| bisphenol A6 (1,1,1,3,3,3-hexafluoro-2,2-bis(4-hydroxyphenyl)propane) | HO—⌬—C(CF₃)₂—⌬—OH |
| bisphenol S (bis(4-hydroxyphenyl)sulfone) | HO—⌬—SO₂—⌬—OH |
| resorcinol | HO—⌬—OH |

The dihalocompound has the formula X—R—X, where each X is a halogen, such as chlorine or bromine, and R is an aliphatic group. As used herein, an aliphatic group of the R group comprises a hydrocarbon chain and may optionally comprise an ether group (—O—) or a siloxane group (—SiR'$_2$—O—, wherein R' is an aliphatic group). The R group may be limited to the hydrocarbon, ether, and siloxane groups. The hydrocarbon chain may be a straight chain alkylene group. Suitable dihalocompounds include those shown in Table 3, as well as those disclosed in the patents listed above.

TABLE 3

| Name | Structure |
|---|---|
| 1,6-dibromohexane | Br—CH₂—CH₂—CH₂—CH₂—CH₂—CH₂—Br |
| bis(2-chloroethyl) ether | Cl—CH₂—CH₂—O—CH₂—CH₂—Cl |
| bis(chloromethyl) tetramethyl disiloxane | Cl—CH₂—Si(CH₃)₂—O—Si(CH₃)₂—CH₂—Cl |

In the first step the dihydroxyaromatic compound is reacted with the dihalocompound to form an oligomer as shown in formula (1). The Ar and R groups may all be the same, all different, or any combination thereof in the oligomer. The dihydroxyaromatic compound is present in an excess amount to form an oligomer with terminal hydroxy groups. As used herein, the oligomer can include a mixture of molecules having different values of n, including unreacted dihydroxyaromatic compound. The oligomer also includes either of both of the hydroxyl form and the ionic form as shown in formula (1). The average value of n depends on the amount of excess dihydroxyaromatic compound. For example, 2:1 molar ratio of dihydroxyaromatic compound to dihalocompound produces an average n of 1 and a 3:2 ratio produces an average n of 2. Methods of performing this reaction are known in the art, including as described in the examples herein and in the above listed patents.

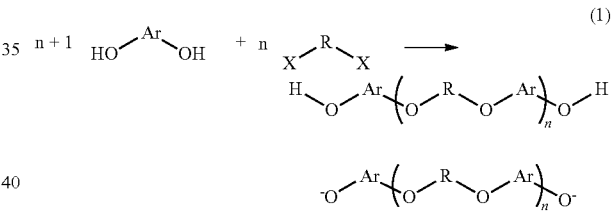

(1)

In the next step, the oligomer is reacted with 4-nitrophthalonitrile to form a phthalonitrile compound as shown in formula (2). Methods of performing this reaction are known in the art, including as described in the examples herein and in the above listed patents.

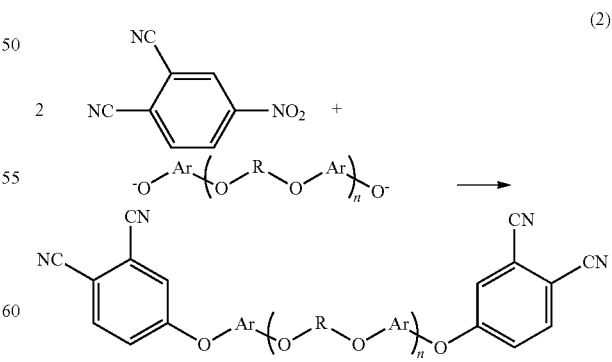

(2)

Optionally, the phthalonitrile compound may be cured with a curing additive to form a thermoset. Such curing agents are known in the art and include, but are not limited to, those disclosed in the patents listed above and those listed in Table 4.

TABLE 4

| Name | Structure |
|---|---|
| bis[4-(4-aminophenoxy)phenyl]sulfone (p-BAPS) | $H_2N$—⟨phenyl⟩—O—⟨phenyl⟩—S(=O)(=O)—⟨phenyl⟩—O—⟨phenyl⟩—$NH_2$ |
| bis[4-(3-aminophenoxy)phenyl]sulfone (m-BAPS) | $H_2N$—⟨3-phenyl⟩—O—⟨phenyl⟩—S(=O)(=O)—⟨phenyl⟩—O—⟨3-phenyl⟩—$NH_2$ |
| 1,4-bis(3-aminophenoxy)benzene (p-APB) | $H_2N$—⟨3-phenyl⟩—O—⟨1,4-phenyl⟩—O—⟨3-phenyl⟩—$NH_2$ |
| 1,3-bis(3-aminophenoxy)benzene (m-APB) | $H_2N$—⟨3-phenyl⟩—O—⟨1,3-phenyl⟩—O—⟨3-phenyl⟩—$NH_2$ |

The following examples are given to illustrate specific applications. These specific examples are not intended to limit the scope of the disclosure in this application.

Example 1

Synthesis of 2:1 Oligomeric Hydroxyl Compound Based on Bisphenol A and 1,6-Dibromohexane Isolated as the Dipotassium Salt To a 2000 mL, three-necked flask fitted with a thermometer and a nitrogen inlet were added bisphenol A (100 g, 0.298 mol), 1,6-dibromohexane (53.4 g, 0.219 mol), powdered anhydrous $K_2CO_3$ (150 g, 1.09 mol), and dimethylsulfoxide (DMSO) (1000 mL). The resulting mixture was degassed with nitrogen at ambient temperature and heated at 90° C. under a nitrogen atmosphere for 8-16 hr. The mixture was cooled and the dipotassium salt of the 2:1 oligomeric hydroxyl compound was left in solution to use in further reactions.

Example 2

Synthesis of 2:1 Oligomeric Phthalonitrile Based on Bisphenol A and 1,6-Dibromohexane in One Reaction Pot To a 2000 mL, three-necked flask fitted with a thermometer and a nitrogen inlet were added bisphenol A (100 g, 0.298 mol), 1,6-dibromohexane (53.4 g, 0.219 mol), powdered anhydrous $K_2CO_3$ (150 g, 1.09 mol), and dimethylsulfoxide (DMSO) (1000 mL). The resulting mixture was degassed with nitrogen at ambient temperature and heated at 90° C. under a nitrogen atmosphere for 8-16 hr. The mixture was cooled to 50° C. At this time, 4-nitrophthalonitrile (77.6 g, 0.449 mol) was added in one portion and the reaction mixture was heated at 80° C. for 6-8 hr. The mixture was allowed to cool to ambient temperature and poured into 1000 mL of distilled water. The mixture was made acidic by the addition of 6 M aqueous HCl and the resin was extracted out of the water layer by toluene (200 mL). The toluene extracts were washed 3 times with 500 mL of distilled water and dried using magnesium sulfate. Removal of the toluene resulted in an amber oil, which was dried at 80° C. under vacuum. The 2:1 oligomeric phthalonitrile was isolated as an amber glassy solid (165 g, 95%). $^1$H-NMR [$CDCl_3$]: λ 7.70 (m, aromatic-HR), 7.31 (m, aromatic-HR), 7.11 (m, aromatic-HR), 7.00 (m, aromatic-HR), 6.80 (m, aromatic-HR), 3.92 (m, aliphatic-HR), 1.78 (m, aliphatic-HR), 1.73 (s, aliphatic-HR), 1.67 (s, aliphatic-HR), 1.61 (s, aliphatic-HR), 1.50 (m, aliphatic-HR).

Example 3

Curing of a 2:1 Oligomeric Phthalonitrile Based on Bisphenol A and 1,6-Dibromohexane with an Aromatic Amine Samples containing the 2:1 oligomeric phthalonitrile from Example 2 and 2-5 weight % of bis[4-(4-aminophenoxy)phenyl]sulfone, bis[4-(3-aminophenoxy)phenyl]sulfone, or 1,3-bis(3-aminophenoxy)benzene (m-APB) were stirred at 200° C. for 2 minutes and cured under nitrogen by heating at 250° C. for 12 hr (overnight) and at 300° C. for 8 hr to afford thermoset polymers. The polymers exhibited excellent thermal stability up to 400° C. before any weight loss was detected. Catastrophic decomposition of the polymers occurred above 375° C. in air.

Example 4

Synthesis of 2:1 Oligomeric Phthalonitrile Based on Bisphenol AF and 1,6-Dibromohexane in One Reaction Pot To a 2000 mL, three-necked flask fitted with a thermometer and a nitrogen inlet were added bisphenol AF (149 g, 0.442 mol), 1,6-dibromohexane (53.4 g, 0.219 mol), powdered anhydrous $K_2CO_3$ (150 g, 1.09 mol), and dimethylsulfoxide (DMSO) (1000 mL). The resulting mixture was degassed with nitrogen at ambient temperature and heated at 90° C. under a nitrogen atmosphere for 8-16 hr. The mixture was cooled to 50° C. At this time, 4-nitrophthalonitrile (80.1 g, 0.463 mol) was added in one portion and the reaction mixture was heated at 80° C. for 6-8 hr. The mixture was allowed to cool to ambient temperature and poured into 1000 mL of distilled water. The mixture was made acidic by the addition of 6 M aqueous HCl and the resin was extracted out of the water layer by toluene (200 mL). The toluene extracts were washed 3 times with 500 mL of distilled water and dried using magnesium sulfate. Removal of the toluene resulted in an amber oil, which was dried at 80° C. under vacuum. The 2:1 oligomeric phthalonitrile was isolated as an amber glassy solid (224 g, 97%). $^1$H-NMR [$CDCl_3$]: λ 7.75 (m, aromatic-HR), 7.32 (m, aromatic-HR), 7.08 (m, aromatic-HR), 6.97 (m, aromatic-HR), 6.81 (m, aromatic-HR), 4.10 (m, aliphatic-HR), 1.80 (m, aliphatic-HR), 1.51 (m, aliphatic-HR).

Example 5

Curing of a 2:1 oligomeric phthalonitrile based on bisphenol AF and 1,6-Dibromohexane with an Aromatic Amine Samples containing the 2:1 oligomeric phthalonitrile from Example 4 and 2-5 weight % of bis[4-(4-aminophenoxy)phenyl]sulfone, bis[4-(3-aminophenoxy)phenyl]sulfone, or 1,3-bis(3-aminophenoxy)benzene (m-APB) were stirred at 200° C. for 2 minutes and cured under nitrogen by heating at 250° C. for 12 hr (overnight) and at 300° C. for 8 hr to afford thermoset polymers. The polymers exhibited excellent thermal stability up to 400° C. before any weight loss was detected. Catastrophic decomposition of the polymers occurred above 375° C. in air.

Example 6

Synthesis of 2:1 Oligomeric Hydroxyl Compound Based on Bisphenol A and Bis(2-Chloroethyl) Ether Isolated as the Dipotassium Salt To a 2000 mL, three-necked flask fitted with a thermometer and a nitrogen inlet were added bisphenol A (100 g, 0.298 mol), bis(2-chloroethyl) ether (31.3 g, 0.219 mol), powdered anhydrous $K_2CO_3$ (150 g, 1.09 mol), and dimethylsulfoxide (DMSO) (1000 mL). The resulting mixture was degassed with nitrogen at ambient temperature and heated at 90° C. under a nitrogen atmosphere for 8-16 hr. The mixture was cooled and the dipotassium salt of the 2:1 oligomeric hydroxyl compound was left in solution to use in further reactions.

Example 7

Synthesis of 2:1 Oligomeric Phthalonitrile Based on Bisphenol A and Bis(2-Chloroethyl) Ether in One Reaction Pot To a 2000 mL, three-necked flask fitted with a thermometer and a nitrogen inlet were added bisphenol A (100 g, 0.298 mol), bis(2-chloroethyl) ether (31.3 g, 0.219 mol), powdered anhydrous $K_2CO_3$ (150 g, 1.09 mol), and dimethylsulfoxide (DMSO) (1000 mL). The resulting mixture was degassed with nitrogen at ambient temperature and heated at 90° C. under a nitrogen atmosphere for 8-16 hr. The mixture was cooled to 50° C. At this time, 4-nitrophthalonitrile (77.7 g, o.449 mol) was added in one portion and the reaction mixture was heated at 80° C. for 6-8 hr. The mixture was allowed to cool to ambient temperature and poured into 1000 mL of distilled water. The mixture was made acidic by the addition of 6 M aqueous HCl and the resin was extracted out of the water layer by toluene (200 mL). The toluene extracts were washed 3 times with 500 mL of distilled water and dried using magnesium sulfate. Removal of the toluene resulted in an amber oil, which was dried at 80° C. under vacuum. The 2:1 oligomeric phthalonitrile was isolated as an amber glassy solid (164 g, 94%). $^1$H-NMR [$CDCl_3$]: λ 7.68 (m, aromatic-HR), 7.27 (m, aromatic-HR), 7.11 (m, aromatic-HR), 6.97 (m, aromatic-HR), 6.81 (m, aromatic-HR), 4.10 (m, aliphatic-HR), 3.88 (m, aliphatic-HR), 1.73 (s, aliphatic-HR), 1.66 (s, aliphatic-HR), 1.59 (s, aliphatic-HR).

Example 8

Curing of a 2:1 Oligomeric Phthalonitrile Based on Bisphenol A and Bis(2-Chloroethyl) Ether with an Aromatic Amine Samples containing the 2:1 oligomeric phthalonitrile from Example 7 and 2-5 weight % of bis[4-(4-aminophenoxy)phenyl]sulfone (p-BAPS), bis[4-(3-aminophenoxy)phenyl]sulfone (m-BAPS), or 1,3-bis(3-aminophenoxy)benzene (m-APB) were stirred at 200° C. for 2 minutes and cured under nitrogen by heating at 250° C. for 12 hr (overnight), 300° C. for 8 hr to afford thermoset polymers. The polymers exhibited excellent thermal stability up to 400° C. before any weight loss was detected. Catastrophic decomposition of the polymers occurred above 375° C. in air.

Example 9

Synthesis of 2:1 Oligomeric Hydroxyl Compound Based on Bisphenol A and Bis(Chloromethyl)Tetramethyl Disiloxane Isolated as the Dipotassium Salt To a 2000 mL, three-necked flask fitted with a thermometer and a nitrogen inlet were added bisphenol A (100 g, 0.298 mol), bis(chloromethyl)tetramethyl disiloxane (50.1 g, 0.217 mol), powdered anhydrous $K_2CO_3$ (150 g, 1.09 mol), and dimethylsulfoxide (DMSO) (1000 mL). The resulting mixture was degassed with nitrogen at ambient temperature and heated at 90° C. under a nitrogen atmosphere for 8-16 hr. The mixture was cooled and the potassium salt of the 2:1 oligomeric hydroxyl compound was left in solution to use in further reactions.

Example 10

Synthesis of 2:1 Oligomeric Phthalonitrile Based on Bisphenol a and Bis(Chloromethyl)Tetramethyl Disiloxane in One Reaction Pot To a 2000 mL, three-necked flask fitted with a thermometer and a nitrogen inlet were added bisphenol A (100 g, 0.298 mol), bis(chloromethyl)tetramethyl disiloxane (50.1 g, 0.217 mol), powdered anhydrous $K_2CO_3$ (150 g, 1.09 mol), and dimethylsulfoxide (DMSO) (1000 mL). The resulting mixture was degassed with nitrogen at ambient temperature and heated at 90° C. under a nitrogen atmosphere for 8-16 hr. The mixture was cooled to 50° C. At this time, 4-nitrophthalonitrile (77.7 g, 0.449 mol) was added in one portion and the reaction mixture was heated at 80° C. for 6-8 hr. The mixture was allowed to cool to ambient temperature and poured into 1000 mL of distilled water. The mixture was made acidic by the addition of 6 M aqueous HCl and the resin was extracted out of the water layer by toluene (200 mL). The toluene extracts were washed 3 times with 500 mL of distilled water and dried using magnesium sulfate. Removal of the toluene resulted in an amber oil, which was dried at 80° C. under vacuum. The 2:1 oligomeric phthalonitrile was isolated as an amber glassy solid (179 g, 94%). $^1$H-NMR [CDCl$_3$]: λ 7.72 (m, aromatic-HR), 7.67 (m, aromatic-HR), 7.34 (m, aromatic-HR), 7.08 (m, aromatic-HR), 6.97 (m, aromatic-HR), 6.86 (m, aromatic-HR), 3.76 (m, aliphatic-HR), 3.50 (m, aliphatic-HR), 1.71 (s, aliphatic-HR), 1.64 (s, aliphatic-HR), 1.61 (s, aliphatic-HR), 0.20 (s, Si—CH$_3$), 0.05 (s, Si–CH$_3$).

Example 11

Curing of a 2:1 Oligomeric Phthalonitrile Based on Bisphenol A and Bis(Chloromethyl)Tetramethyl Disiloxane with an Aromatic Amine Samples containing the 2:1 oligomeric phthalonitrile from Example 10 and 2-5 weight % of bis[4-(4-aminophenoxy)phenyl]sulfone (p-BAPS), bis[4-(3-aminophenoxy)phenyl]sulfone (m-BAPS), or 1,3-bis(3-aminophenoxy)benzene (m-APB) were stirred at 200° C. for 2 minutes and cured under nitrogen by heating at 250° C. for 12 hr (overnight) and at 300° C. for 8 hr to afford thermoset polymers. The polymers exhibited excellent thermal stability up to 400° C. before any weight loss was detected. Catastrophic decomposition of the polymers occurred above 375° C. in air.

Example 12

Synthesis of 2:1 Oligomeric Phthalonitrile Based on 1,3-Dihydroxybenzene (Resorcinol) and Bis(Chloromethyl)Tetramethyl Disiloxane in One Reaction Pot To a 2000 mL, three-necked flask fitted with a thermometer and a nitrogen inlet were added 1,3-dihydroxybenzene (48.2 g, 0.438 mol), bis(chloromethyl)tetramethyl disiloxane (50.1 g, 0.217 mol), powdered anhydrous K$_2$CO$_3$ (150 g, 1.09 mol), and dimethylsulfoxide (DMSO) (1000 mL). The resulting mixture was degassed with nitrogen at ambient temperature and heated at 90° C. under a nitrogen atmosphere for 8-16 hr. The mixture was cooled to 50° C. At this time, 4-nitrophthalonitrile (76.1 g, 0.440 mol) was added in one portion and the reaction mixture was heated at 80° C. for 6-8 hr. The mixture was allowed to cool to ambient temperature and poured into 1000 mL of distilled water. The mixture was made acidic by the addition of 6 M aqueous HCl and the resin was extracted out of the water layer by toluene (200 mL). The toluene extracts were washed 3 times with 500 mL of distilled water and the toluene extracts were dried using magnesium sulfate. Removal of the toluene resulted in an amber oil, which was dried at 80° C. under vacuum. The 2:1 oligomeric phthalonitrile was isolated as an amber glassy solid (131 g, 95%).

$^1$H-NMR [CDCl$_3$]: λ 7.70 (m, aromatic-HR), 7.69 (m, aromatic-HR), 7.35 (m, aromatic-HR), 7.10 (m, aromatic-HR), 6.98 (m, aromatic-HR), 6.88 (m, aromatic-HR), 3.73 (m, aliphatic-HR), 3.46 (m, aliphatic-HR), 0.22 (s, Si—CH$_3$), 0.06 (s, Si—CH$_3$).

Example 13

Curing of a 2:1 Oligomeric Phthalonitrile Based on 1,3-Dihydroxybenzene (Resorcinol) and Bis(Chloromethyl)Tetramethyl Disiloxane with an Aromatic Amine Samples containing the 2:1 oligomeric phthalonitrile from Example 12 and 2-5 weight % of bis[4-(4-aminophenoxy)phenyl]sulfone (p-BAPS), bis[4-(3-aminophenoxy)phenyl]sulfone (m-BAPS), or 1,3-bis(3-aminophenoxy)benzene (m-APB) were stirred at 200° C. for 2 minutes and cured under nitrogen by heating at 250° C. for 12 hr (overnight) and at 300° C. for 8 hr to afford thermoset polymers. The polymers exhibited excellent thermal stability up to 400° C. before any weight loss was detected. Catastrophic decomposition of the polymers occurred above 375° C. in air.

Obviously, many modifications and variations are possible in light of the above teachings. It is therefore to be understood that the claimed subject matter may be practiced otherwise than as specifically described. Any reference to claim elements in the singular, e.g., using the articles "a", "an", "the", or "said" is not construed as limiting the element to the singular.

What is claimed is:

1. A phthalonitrile compound having the formula:

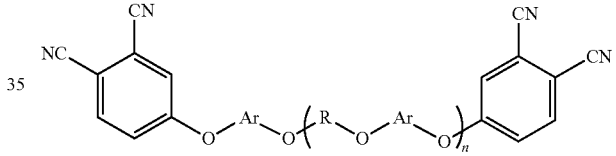

wherein n is a positive integer;
wherein each R comprises a hydrocarbon chain optionally comprising —O— or —SiR'$_2$—O—;
wherein each R' is an aliphatic group; and
wherein each Ar is an aromatic group with the proviso that Ar comprises at least two aromatic rings when n is 1 and R is an alkylene group.

2. The phthalonitrile compound of claim 1, wherein each Ar is —C$_6$H$_4$—C(CH$_3$)$_2$—C$_6$H$_4$—, —C$_6$H$_4$—C(CF$_3$)$_2$—C$_6$H$_4$—, or —C$_6$H$_4$—SO$_2$—C$_6$H$_4$—.

3. The phthalonitrile compound of claim 1, wherein each Ar is m-phenylene.

4. The phthalonitrile compound of claim 1, wherein each R is an alkylene group or hexylene.

5. The phthalonitrile compound of claim 1, wherein each R is —C$_2$H$_4$—O—C$_2$H$_4$—.

6. The phthalonitrile compound of claim 1, wherein each R is
—CH$_3$—Si(CH$_3$)$_2$—O—Si(CH$_3$)$_2$—CH$_3$—.

7. The phthalonitrile compound of claim 1, wherein the phthalonitrile compound is:

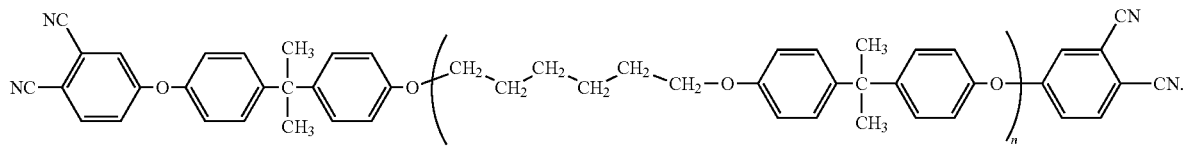

8. The phthalonitrile compound of claim 1, wherein the phthalonitrile compound is:

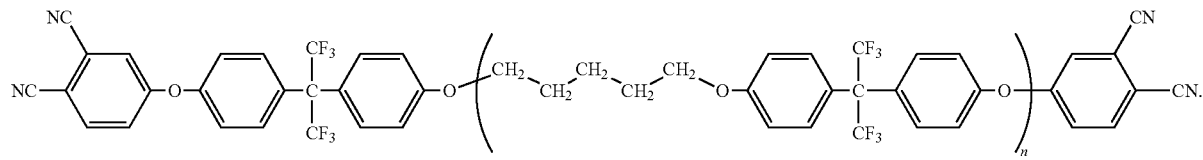

ks9. The phthalonitrile compound of claim 1, wherein the phthalonitrile compound is:

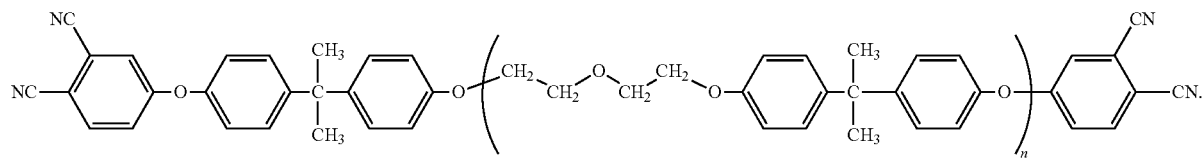

10. The phthalonitrile compound of claim 1, wherein the phthalonitrile compound is:

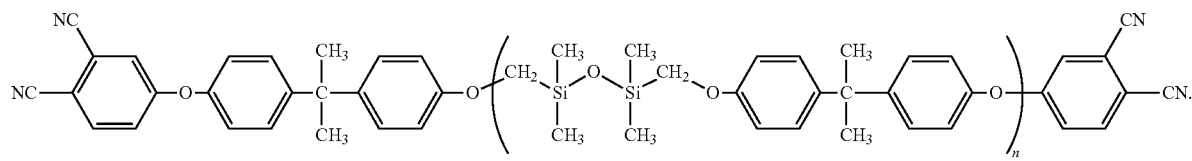

11. The phthalonitrile compound of claim 1, wherein the phthalonitrile compound is:

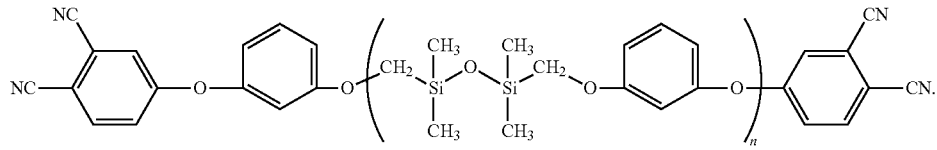

12. A method comprising:
curing the phthalonitrile compound of claim 1 with a curing additive to form a thermoset.

13. The method of claim 12, wherein the curing additive is bis(3-[4-aminophenoxy]phenyl)sulfone, bis[4-(4-aminophenoxy) phenyl]sulfone, 1,4-bis(3-aminophenoxy)benzene, or 1,3-bis(3-aminophenoxy)benzene.

14. A method comprising:
reacting an excess of a dihydroxyaromatic compound having the formula HO—Ar—OH with a dihalocompound having the formula X—R—X to form an oligomer having the formula

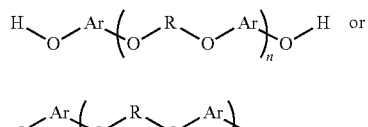

wherein each X is a halide;
wherein each R comprises a hydrocarbon chain optionally comprising —O— or —SiR'$_2$—O—;
wherein each R' is an aliphatic group; and
wherein each Ar is an aromatic group; and
reacting the oligomer with 4-nitrophthalonitrile to form a phthalonitrile compound having the formula:

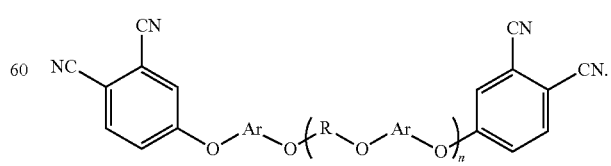

15. The method of claim 14, wherein the phthalonitrile compound is:

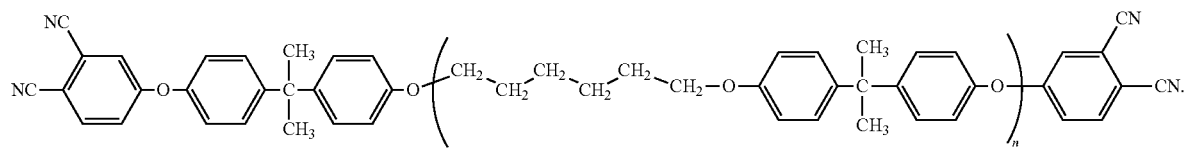
16. The method of claim 14, wherein the phthalonitrile compound is:
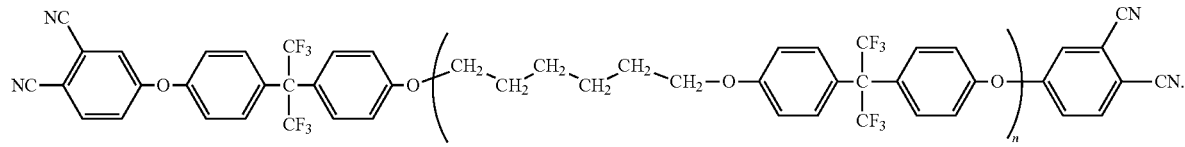
17. The method of claim 14, wherein the phthalonitrile compound is:
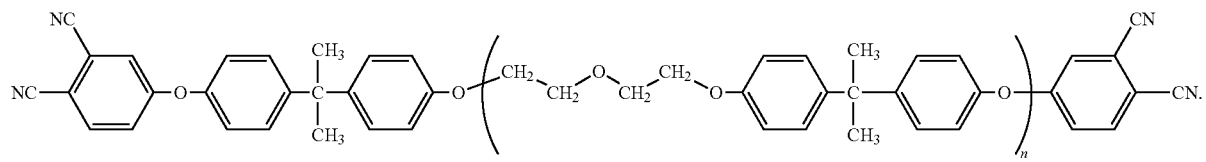
18. The method of claim 14, wherein the phthalonitrile compound is:
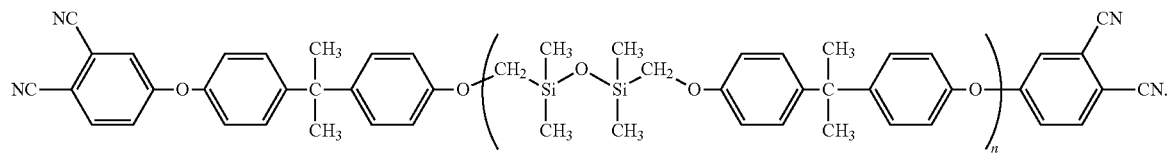
19. The method of claim 14, wherein the phthalonitrile compound is:
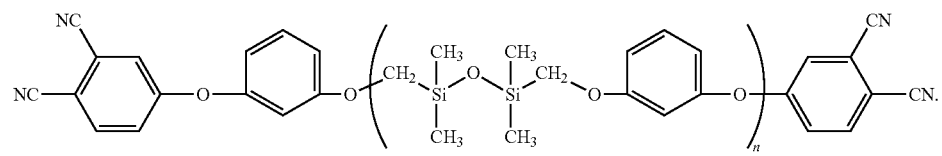
20. The method of claim 14, further comprising:
curing the phthalonitrile compound with a curing additive to form a thermoset.
* * * * *